(12) United States Patent
Yamamoto et al.

(10) Patent No.: US 7,858,567 B2
(45) Date of Patent: Dec. 28, 2010

(54) SKIN CLEANSING COMPOSITIONS

(75) Inventors: Naoko Yamamoto, Tokyo (JP); Ryosuke Fujii, Wakayama (JP); Masaki Shimizu, Tokyo (JP)

(73) Assignee: Kao Corporation, Tokyo (JP)

( * ) Notice: Subject to any disclaimer, the term of this patent is extended or adjusted under 35 U.S.C. 154(b) by 237 days.

(21) Appl. No.: 12/104,200

(22) Filed: Apr. 16, 2008

(65) Prior Publication Data

US 2008/0261845 A1 Oct. 23, 2008

(30) Foreign Application Priority Data

Apr. 20, 2007 (JP) .............. 2007-111423
Apr. 20, 2007 (JP) .............. 2007-111424

(51) Int. Cl.
*A61K 7/00* (2006.01)

(52) U.S. Cl. .............. 510/130; 510/137; 510/159; 510/424; 510/471

(58) Field of Classification Search .............. None
See application file for complete search history.

(56) References Cited

U.S. PATENT DOCUMENTS

| 5,057,311 | A | 10/1991 | Kamegai et al. |
| 6,312,678 | B1 | 11/2001 | Elliott et al. |
| 6,444,629 | B1 | 9/2002 | Elliott et al. |
| 2007/0269397 | A1* | 11/2007 | Terada .............. 424/70.12 |

FOREIGN PATENT DOCUMENTS

| JP | 02-042013 | 2/1990 |
| JP | 09-165598 | 6/1997 |
| JP | 2001-513538 | 9/2001 |
| JP | 2001-513539 | 9/2001 |

OTHER PUBLICATIONS

U.S. Appl. No. 12/115,206, filed May 5, 2008, Yamamoto, et al.

* cited by examiner

*Primary Examiner*—Necholus Ogden, Jr.
(74) *Attorney, Agent, or Firm*—Oblon, Spivak, McClelland, Maier & Neustadt, L.L.P.

(57) ABSTRACT

A skin cleansing composition contains the following ingredients (A), (B) and (C):
(A) a polyoxyethylene alkylether sulfate,
(B) a polyoxyethylene alkylether carboxylate, and
(C) a cationic group-containing polymer having a cationic charge density of not less than 4.5 meq/g, and/or polyvinylpyrrolidone. A weight ratio (A):(B) of the ingredient (A) to the ingredient (B) is from 85:15 to 25:75. A total content of the ingredients (A) and (B) based on the whole composition ranges from 5 to 25 wt %. A content of the ingredient (C) ranges from 0.05 to 1 wt %. The skin cleansing composition is excellent in foamability and foam quality, and provides a good stop feeling during rinsing and a refreshed touch feeling after towel blotting.

21 Claims, No Drawings

SKIN CLEANSING COMPOSITIONS

FIELD OF THE INVENTION

The present invention relates to skin cleansing compositions.

BACKGROUND OF THE INVENTION

Among various performances required for skin cleansing compositions for cleansing the face and body, a frictional feeling (stop feeling) is important as a feeling to the touch during rinsing upon its use. The shorter the speed until this stop feeling can be sensed in the course of rinsing and the stronger the stop feeling, the more preferred because a refreshed clean feeling is given.

Skin cleansing compositions which contain a polyoxyethylene alkylether sulfate, a surfactant commonly employed in the present field of art, as a main ingredient have conventionally been accompanied by a problem in that a slimy feeling remains after rinsing, although they have good lathering ability. JP-A-2001-513539 and JP-A-2001-513538 disclose that an improved rinse feeling is available upon rinsing when a water-insoluble oil such as polyisobutene or silicone oil is added to a personal cleansing composition containing, as a main ingredient, a water-soluble surfactant such as a polyoxyethylene alkylether sulfate. However, the addition of an oil ingredient to a skin cleansing composition as mentioned above involves such a problem that, especially when used to cleanse the body, a stop feeling is not sufficient upon rinsing and a residual feeling of the oil ingredient on the skin and its oily feeling remain strong after being rinsed off, and therefore, the skin remains tacky and no refreshed feeling to the touch is available.

In JP-A-02-042013 and JP-A-09-165598, cleansing compositions containing a specific surfactant and a cationic polymer are disclosed. In hair cleansers, such cationic polymers are employed as conditioning agents for reducing a frictional feeling, and improves finger combing upon rinsing. They are also used as conditioning agents in skin cleansers to moisturize the skin. In skin cleansing applications, however, these cleansing compositions are not fully satisfactory in view of a stop feeling upon rinsing.

SUMMARY OF THE INVENTION

The present invention relates to a skin cleansing composition containing the following ingredients (A), (B) and (C):

(A) a polyoxyethylene alkylether sulfate,
(B) a polyoxyethylene alkylether carboxylate, and
(C) a cationic group-containing polymer having a cationic charge density of not less than 4.5 meq/g, and/or polyvinylpyrrolidone, wherein a weight ratio (A):(B) of the ingredient (A) to the ingredient (B) is from 85:15 to 25:75, a total content of the ingredients (A) and (B) based on the whole composition ranges from 5 to 25 wt %, and a content of the ingredient (C) ranges from 0.05 to 1 wt %.

The skin cleansing composition according to the present invention is fast in lathering, excellent in both foam volume and foam quality, is good in providing a stop feeling upon rinsing, and provides a refreshed feeling after towel blotting. When polyvinylpyrrolidone is included, its pearly appearance is improved further. When a higher fatty acid or higher alcohol is included, good foam vanishing at the drain can be provided upon rinsing a used body towel and washing or rinsing out the foam.

DETAILED DESCRIPTION OF THE INVENTION

The present invention relates to a skin cleansing composition, which is excellent in foamability and foam quality, is good in providing a stop feeling upon rinsing, and provides a refreshed feeling after towel blotting.

The present inventors found that a skin cleansing composition equipped with the above-described properties can be obtained from the combined use of a polyoxyethylene alkylether sulfate, a polyoxyethylene alkylether carboxylate, and a specific cationic group-containing polymer or polyvinylpyrrolidone.

As an example of the polyoxyethylene alkylether sulfate employed as the ingredient (A) in the present invention, one represented by the following formula is preferred.

$$R-O(CH_2CH_2O)_n-SO_3X$$

wherein R represents an alkyl or alkenyl group having from 10 to 18 carbon atoms, n stands for a number of from 0.5 to 5 on average, and X represents a hydrogen atom, alkali metal, alkaline earth metal, ammonium or organic ammonium.

In the formula, an alkyl group having from 12 to 14 carbon atoms may be preferred as R. The average number of moles of added ethylene oxide may range from 0.5 to 5, with from 1 to 4 being more preferred.

As X, on the other hand, an alkali metal such as sodium or potassium; an alkaline earth metal such as calcium or magnesium; ammonium; an ammonium derived from an alkanolamine such as monoethanolamine, diethanolamine or triethanolamine; a cation derived from a basic amino acid such as arginine or lysine may be mentioned.

One or more polyoxyethylene alkylether sulfates may be used as the ingredient (A). The ingredient (A) may be contained at preferably from 1 to 20 wt %, more preferably from 3 to 13 wt % for fast lathering, excellent foam volume and superb stop feeling upon rinsing.

As the polyoxyethylene alkylether carboxylate employed as the ingredient (B), one represented by the following formula is preferred.

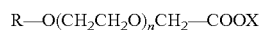

$$R-O(CH_2CH_2O)_nCH_2-COOX$$

wherein R represents an alkyl or alkenyl group having from 10 to 18 carbon atoms, n stands for a number of from 0.5 to 10 on average, and X represents a hydrogen atom, alkali metal, alkaline earth metal, ammonium or organic ammonium.

In the formula, an alkyl group having from 12 to 16 carbon atoms may be more preferred as R. The average number of moles of added ethylene oxide may range from 0.5 to 10, with from 1 to 6 being more preferred.

As X, on the other hand, an alkali metal such as sodium or potassium; an alkaline earth metal such as calcium or magnesium; ammonium; an ammonium derived from an alkanolamine such as monoethanolamine, diethanolamine or triethanolamine; a cation derived from a basic amino acid such as arginine or lysine may be mentioned.

One or more polyoxyethylene alkylether carboxylates may be used as the ingredient (B). The ingredient (B) may be contained at preferably from 1 to 20 wt %, more preferably from 1.5 to 10 wt % for excellent foam volume and foam quality and superb stop feeling upon rinsing.

In the present invention, the weight ratio (A):(B) of the ingredient (A) to the ingredient (B) is from 85:15 to 25:75, with from 75:25 to 35:65 being preferred. This range is preferred because of the availability of excellent lathering, foam volume and foam quality and superb stop feeling upon rinsing.

Further, the total content of the ingredients (A) and (B) in the whole composition is from 5 to 25 wt %, with from 7.5 to 20 wt % being preferred. This range is preferred because of the availability of excellent lathering, foam volume and foam quality.

In the present invention, the cationic group-containing polymer, the cationic charge density of which is not less than 4.5 meq/g, and/or polyvinylpyrrolidone is also used as the ingredient (C) in combination with the above-described ingredients (A) and (B).

It is to be noted that the term "cationic charge density" as used herein means the number (meq/g) of equivalents of cationic charges in monomer units which constitute a polymer.

The cationic charge density of the cationic group-containing polymer is not less than 4.5 meq/g, preferably from 4.5 to 7, more preferably from 5 to 7, even more preferably from 5.5 to 6.5. With one having a high cationic charge density in this range, a good stop feeling is available upon rinsing the cleansing composition. More preferred is an amphoteric polymer also containing anionic groups in addition to such cationic groups.

Among such cationic group-containing polymers having a cationic charge density of not less than 4.5 meq/g, examples include homopolymer of dimethyldiallylammonium chloride; copolymers of dimethyldiallylammonium chloride with other monomers such as (meth)acrylic acid, (meth)acrylate esters and (meth)acrylamides; and polychloromethacryloyloxyethyltrimethylammonium chloride.

More specific examples include homopolymer of dimethyldiallylammonium chloride ("MERQUAT 100", trade name; product of Ondeo Nalco Co.; charge density: 6.2 meq/g), a copolymer of dimethyldiallylammonium chloride and acrylic acid ("MERQUAT 295", trade name; product of Ondeo Nalco Co.; charge density: 6.0 meq/g); another copolymer of dimethyldiallylammonium chloride and acrylic acid ("MERQUAT 280", trade name; product of Ondeo Nalco Co.; charge density: 5.0 meq/g); and polychloromethacryloyloxyethyltrimethylammonium chloride (product of Kao Corporation; charge density: 4.8 meq/g).

The homopolymer of dimethyldiallylammonium chloride and the copolymers of dimethyldiallylammonium chloride and acrylic acid are preferred from the standpoint of the corrosion resistance of production facilities. The copolymer in which the polymerization ratio of dimethyldiallylammonium chloride to acrylic acid is 97:3 ("MERQUAT 295", trade name; product of Ondeo Nalco Co.; charge density: 6.0 meq/g) is more preferred from the standpoints of stop feeling upon rinsing and foam volume.

As polyvinylpyrrolidone in the ingredient (C), on the other hand, one having a K-value of from 10 to 100, desirably from 15 to 90 is preferred because of a better stop feeling upon rinsing. It is to be noted that the term "K-value" as used herein means a value called "intrinsic viscosity" and obtained from the Fikentscher's equation that expresses the viscosity of a polyvinylpyrrolidone solution as a function of concentration. Brands of polyvinylpyrrolidone are indicated by their K-values, which serve as rough indications of their molecular weights.

As the ingredient (C), one or more of cationic group-containing polymers, the cationic charge densities of which are not less than 4.5 meq/g, and polyvinylpyrrolidone may be used. It may also be possible to use a cationic group-containing polymer, the cationic charge density of which is not less than 4.5 meq/g, and polyvinylpyrrolidone in combination. The ingredient (C) is contained at from 0.05 to 1 wt %, preferably from 0.075 to 1 wt %, in the whole composition. This range is preferred for excellent stop feeling upon rinsing.

When a cationic group-containing polymer, the cationic charge density of which is not less than 4.5 meq/g, and polyvinylpyrrolidone are used in combination as the ingredient (C), their weight ratio, that is, the weight ratio of the cationic group-containing polymer whose cationic charge density is not less than 4.5 meq/g to polyvinylpyrrolidone may range preferably from 90:10 to 20:80, more preferably from 80:20 to 25:75 because of a good stop feeling upon rinsing and a good liquid appearance.

The skin cleansing composition according to the present invention may further contain (D) an inorganic salt or an organic acid salt having not more than 6 carbon atoms. Examples of the inorganic salt include salts between alkali metals or alkaline earth metals and halogens, sulfuric acid, sulfurous acid, phosphoric acid and the like. Specifically, sodium chloride, potassium chloride, sodium bromide, magnesium chloride, sodium sulfate, potassium sulfate, sodium dihydrogenphosphate, disodium hydrogenphosphate and the like can be mentioned. Examples of the organic acid salt include salts between acetic acid and hydroxy acids or polyacids, such as lactic acid, malic acid, citric acid and succinic acid, and alkali metals or the like. Among these, preferred are sodium chloride, sodium malate, sodium lactate, sodium citrate, and sodium succinate.

As the ingredient (D), one or more of such inorganic salts and organic acid salts can be used within the range not lacking a foamability and foam quality as effects of the present invention. An inclusion of the ingredient (D) at from 0.5 to 10 wt %, desirably at from 0.5 to 6 wt % in the whole composition can facilitate the dissolution of a sparingly soluble complex formed of the three ingredients (A), (B) and (C) (especially a cationic group-containing polymer having a cation charge density of not less than 4.5 meq/g) and can provide an improved stop feeling and liquid appearance (clarity), and therefore, is preferred.

In the present invention, the weight ratio (A):(B) of the ingredient (A) to the ingredient (B) ranges from 85:15 to 25:75. At this weight ratio, the dissolution of the complex formed of the three ingredients (A), (B) and (C) is facilitated. When the value of (C)/((A)+(B)) is from 0.025 to 0.08, the complex becomes more soluble.

Further, the inclusion of the inorganic acid or the organic acid salt having not more than 6 carbon atoms still further facilitates the dissolution of the complex formed of the three ingredients (A), (B) and (C). A (D)/((A)+(B)+(C)) value of from 0.19 to 0.34 is more preferred, because the solubility is increased and the stability and pearly luster can be shown more easily. The dissolved complex precipitates in the course of dilution and is adsorbed on the skin. It is preferred for the complex to have high solubility, because the dissolved complex precipitates in the course of dilution and is adsorbed on the skin, and therefore, the sliminess promptly vanishes and the stop feeling is improved further. A combination of the ingredient (A), the ingredient (B), the cation group-containing polymer having the cationic charge density of not less than 4.5 meq/g (C) and the inorganic salt (D) is more preferred.

The skin cleansing composition according to the present invention can further contain a higher fatty acid and/or higher alcohol as an ingredient (E). It is to be noted that the higher fatty acid and higher alcohol may each be a linear one having preferably from 10 to 18 carbon atoms, more preferably from 12 to 15 carbon atoms.

The inclusion of the ingredient (E) can generally reduce the volume of foam at a dilution rate higher than that of a body cleanser, and therefore, can facilitate the vanishing (rinsability) of foam remaining on a used body towel and also the vanishing (drainability) of foam remaining in the drain after being rinsed off from the body.

Further, the skin cleansing composition according to the present invention may preferably show a pH in a weakly acidic to neutral range as will be described subsequently herein. In such a composition, the higher fatty acid is contained as a lipid (free fatty acid) rather than a fatty acid soap as a salt in the composition, and therefore, is considered to generally contribute to an improvement in foam performance such as foam quality in a dilution rate range for body cleansing.

As the ingredient (E), one or more of higher fatty acids and higher alcohols can be used. It is also possible to use a higher fatty acid and a higher alcohol in combination. Combined use of lauric acid and myristyl alcohol is preferred in that this combination has good foam rinsing/draining effects while improving foam performance.

The ingredient (E) may be contained at preferably from 0.3 to 3 wt %, more preferably from 0.5 to 2 wt % in the whole composition.

The skin cleansing composition according to the present invention can further contain a pearlescence-imparting agent as an ingredient (F).

Examples of the pearlescence-imparting agent include (mono/di) esters of fatty acids having from 16 to 22 carbon atoms with ethylene glycol and esters of fatty acids having from 16 to 22 carbon atoms with polyethylene glycols having (1-7) polyoxyethylene units. (Mono/di) ethylene glycol esters of fatty acids having from 16 to 18 carbon atoms are preferred.

More specific examples include ethylene glycol monofatty acid esters such as ethylene glycol monostearate and ethylene glycol monobehenate; and ethylene glycol di-fatty acid esters such as ethylene glycol distearate and ethylene glycol dibehenate.

Such pearlescence-imparting agents can be used either singly or in combination. The ingredient (F) may be contained at preferably from 1 to 3 wt %, more preferably from 1.5 to 2.5 wt % in the whole composition, in terms of a good pearly luster.

In addition to the above-described ingredients, the skin cleansing composition according to the present invention may also contain one or more of other surfactants employed in usual cleansing compositions to the extent not impairing the effects of the present invention. Specific examples include anionic surfactants such as alkylbenzenesulfonates, α-olefinsulfonates, alkanesulfonates, α-sulfofatty acid esters, acylated amino acids, monoalkyl phosphates and acyl-L-glutamates; nonionic surfactants such as polyoxyalkylene alkyl ethers, alkyl glucosides, fatty acid mono- or di-alkanolamides, polyoxyalkylene block polymers, glycerin fatty acid esters and alkyl glyceryl ethers; cationic surfactants such as quaternary ammonium salts; and amphoteric surfactants such as carbobetaines, sulfobetaines, imidazolinium betaines, hydroxybetaines and fatty acid amidobetaines.

The skin cleansing composition according to the present invention may further contain one or more of various ingredients, which are commonly employed in cleansing compositions, as needed. Specifically, it is possible to contain, for example, one or more of humectants such as propylene glycol, dipropylene glycol, glycerin and sorbitol; solvents such as water and ethanol; viscosity adjusters such as methylcellulose; antimicrobial agents such as triclosan and trichlorcarban; anti-inflammatories such as potassium glycyrrhizinate and tocopherol acetate; preservatives such as methylparaben, butylparaben, phenoxyethanol and benzoate salts; and in addition, colorants, fragrances, ultraviolet absorbers, antioxidants and the like, as needed.

The skin cleansing composition according to the present invention can be prepared in a manner known per se in the art by weighing the ingredients and mixing them in a desired order in water or an aqueous medium composed mainly of water and containing another water-soluble solvent such as an alcohol. It can be applied as a body shampoo, facial wash, makeup remover or the like.

The skin cleansing composition according to the present invention may preferably be adjusted to weakly acidic, because it gives reduced irritation to the skin, shows good lathering upon cleansing without an impairment of excellent cleansing power, and is excellent in stop feeling upon rinsing and in use feeling.

The term "weakly acidic" as used herein means a pH of from 4.5 to 7, preferably a pH of from 4.5 to 6.5, and in the present invention, each pH indicates a value at 25° C. when diluted to 20-fold by weight with deionized water.

The following examples further describe and demonstrate embodiments of the present invention. The examples are given solely for the purpose of illustration and are not to be construed as limitations of the present invention.

EXAMPLES

Examples 1-32 & Comparative Examples 1-13

Skin cleansing compositions of the formulas shown in Table 1 to Table 9 were prepared, and were assessed for the speed until a stop feeling was sensed in the course of rinsing, the strength of the stop feeling upon completion of rinsing, a refreshed feeling after towel blotting and the volume of foam. In some of the examples, the skin cleansing compositions were also assessed for a smooth feeling after drying, a pearly appearance, foam vanishing, and a liquid appearance. The results are also shown in Table 1 to Table 9, respectively. Meanwhile, the blending quantity of each polymer was indicated as the value of each polymer solid.

(Preparation Procedure)

In each example or comparative example, the ingredients shown in the corresponding table were weighed and added into deionized water, followed by thorough stirring at 50° C. to afford the skin cleansing composition. Sodium hydroxide or malic acid was added as much as needed to adjust the pH of its 20-fold dilution to become weakly acidic. It is to be noted that the pH was measured using a pH meter (manufactured by Horiba, Ltd., Model No.: F-22) after the composition was diluted to 20-fold with deionized water to obtain a 5 wt % aqueous solution.

(Assessment Methods)

(1) Speed Until a Stop Feeling was Sensed in the Course of Rinsing (Forearm Cleansing Assessment)

After each cleansing composition (1.0 g) was applied to one hand, diluted with tap water and lathered, both arms (forward of the elbows) were cleansed and were then rinsed with tap water. At that time, the rinsing was conducted while rubbing both arms together, and the number of rubbing until a stop feeling was sensed was counted. The count results were ranked in accordance with the following assessment standards.

5: number of rubbing<3
4: 3≦number of rubbing<6
3: 6≦number of rubbing<9
2: 9≦number of rubbing<12
1: 12≦number of rubbing (2) Strength of a Stop Feeling Upon Completion of Rinsing (Body Cleansing Assessment)

Using each cleansing composition, ten (10) expert assessors cleansed the body once a day. The cleansing was conducted for 3 days running, and an assessment was performed for the strength of a stop feeling upon completion of rinsing. The results determined based on the overall assessment over the 3 days were indicated in accordance with the following standards.

A: number of assessors replied "a strong stop feeling" upon completion of rinsing: ≧8
B: number of assessors replied "a strong stop feeling" upon completion of rinsing: 5 to 7
C: number of assessors replied "a strong stop feeling" upon completion of rinsing: 2 to 4
D: number of assessors replied "a strong stop feeling" upon completion of rinsing: 0 or 1

(3) Refreshed Feeling After Towel Blotting (Body Cleansing Assessment)

Using each cleansing composition, ten (10) expert assessors cleansed the body once a day. The cleansing was conducted for 3 days running, and an assessment was performed for a refreshed feeling after towel blotting. The results determined based on the overall assessment over the 3 days were indicated in accordance with the following standards.

A: number of assessors replied "refreshed" after towel blotting: ≧8
B: number of assessors replied "refreshed" after towel blotting: 5 to 7
C: number of assessors replied "refreshed" after towel blotting: 2 to 4
D: number of assessors replied "refreshed" after towel blotting: 0 or 1

(4) The Volume of Foam

The cleansing composition prepared in each example or comparative example was diluted with hard water (hardness: 4 mg/L) to 150-fold (equivalent to the condition upon cleansing the body) to provide a sample aqueous solution. The sample aqueous solution (7.5 mL) was placed in a graduated 50-mL glass cylinder equipped with a stopper cock, and the stopper cock was put thereon. Using a shaker (manufactured by Iwaki Sangyo K. K.; Model No.: "UNIVERSAL SHAKER V-SX", trade name), the cylinder was shaken at a rate of 300 strokes/min, and immediately after the completion of the shaking, the volume of foam was read.

(5) Smooth Feeling After Drying

Using each cleansing composition, ten (10) expert assessors cleansed the body once a day. The cleansing was conducted for 3 days running, and an assessment was performed for a smooth feeling after drying. The results determined based on the overall assessment over the 3 days were indicated in accordance with the following standards.

A: number of assessors replied "smooth" after drying: ≧8
B: number of assessors replied "smooth" after drying: 5 to 7
C: number of assessors replied "smooth" after drying: 2 to 4
D: number of assessors replied "smooth" after drying: 0 or 1

(6) Pearly Appearance

Visually assessed was an appearance, specifically a pearly lustrous appearance when each cleansing composition was placed in a glass bottle. The assessment results were ranked in accordance with the following standards.

A: Discernable pearly lustrous appearance
B: Less discernable pearly lustrous appearance
C: No pearly lustrous appearance (7) Foam Drainability The cleansing composition prepared in each example or comparative example was diluted with hard water (hardness: 4 mg/L) at a high dilution rate (400-fold), which was set in view of drainability after rinsing, to provide a sample aqueous solution. The sample aqueous solution (7.5 mL) was placed in a graduated 50-mL glass cylinder equipped with a stopper cock, and the stopper cock was put thereon. Using the shaker (manufactured by Iwaki Sangyo K. K.; Model No.: "UNIVERSAL SHAKER V-SX", trade name), the cylinder was shaken at a rate of 300 strokes/min, and immediately after the completion of the shaking, the volume (cm) of foam was read.

(8) Liquid Appearance

Visually assessed was an appearance (clarity) when each cleansing composition was placed in a glass bottle. The assessment results were ranked in accordance with the following standards.

A: Discernable clarity
B: Less discernable clarity
C: No clarity

TABLE 1

| | Ingredients (wt %) | Examples | | | Comparative Examples | | | |
|---|---|---|---|---|---|---|---|---|
| | | 1 | 2 | 3 | 1 | 2 | 3 | 4 |
| A | Sodium polyoxyethylene(2) laurylether sulfate | 7.5 | 5.0 | 3.5 | 10.0 | | 10.0 | |
| B | Polyoxyethylene(4.5) laurylether carboxylic acid | 2.5 | 5.0 | 6.5 | | 10.0 | | 10.0 |
| C | Diallyldimethylammonium chloride-acrylic acid (97:3) copolymer (cationic charge density: 6.0 meq/g) *1 | 0.5 | 0.5 | 0.5 | | | 0.5 | 0.5 |
| | Sodium hydroxide (48%) | 0.3 | 0.6 | 0.8 | | 1.3 | | 1.3 |
| | Malic acid (50%) | | | | 0.1 | | 0.1 | |
| | Deionized water | Balance | Balance | Balance | Balance | Balance | Balance | Balance |
| | Total | 100 | 100 | 100 | 100 | 100 | 100 | 100 |
| | pH | 6.2 | 6.2 | 6.2 | 6.2 | 6.2 | 5.7 | 6.4 |
| | (A):(B) | 75:25 | 50:50 | 35:65 | 100:0 | 0:100 | 100:0 | 0:100 |
| | Speed until stop feeling was sensed in the course of rinsing | 4 | 4 | 4 | 2 | 3 | 4 | 1 |
| | Strength of stop feeling upon completion of rinsing | B | A | B | D | C | C | C |
| | Refreshed feeling after towel blotting | B | B | B | D | C | C | C |
| | Foam volume (cm) | 3.0 | 4.4 | 2.8 | 2.4 | 1.6 | 2.0 | 2.5 |

*1: MERQUAT 295 (trade name); Product of Ondeo Nalco Co.

TABLE 2

|   | Ingredients (wt %) | Examples 4 | Examples 5 | Examples 6 | Comparative Examples 5 | Comparative Examples 6 |
|---|---|---|---|---|---|---|
| A | Sodium polyoxyethylene(2) laurylether sulfate | 11.25 | 7.5 | 5.25 | 15.0 | |
| B | Polyoxyethylene(4.5) laurylether carboxylic acid | 3.75 | 7.5 | 9.75 | | 15.0 |
| C | Diallyldimethylammonium chloride-acrylic acid (97:3) copolymer (cationic charge density: 6.0 meq/g) *1 | 0.4 | 0.4 | 0.4 | 0.4 | 0.4 |
|   | Sodium hydroxide (48%) | 0.5 | 0.9 | 1.2 | | 1.8 |
|   | Malic acid (50%) | | | | 0.1 | |
| D | Sodium chloride | 4.0 | 4.0 | 4.0 | 4.0 | 4.0 |
|   | Deionized water | Balance | Balance | Balance | Balance | Balance |
|   | Total | 100 | 100 | 100 | 100 | 100 |
|   | pH | 6.2 | 6.2 | 6.2 | 5.7 | 6.4 |
|   | (A):(B) | 75:25 | 50:50 | 35:65 | 100:0 | 0:100 |
|   | Speed until stop feeling was sensed in the course of rinsing | 5 | 5 | 4 | 4 | 1 |
|   | Strength of stop feeling upon completion of rinsing | B | A | A | C | C |
|   | Refreshed feeling after towel blotting | A | A | A | C | C |
|   | Liquid appearance | B | A | A | C | A |

*1: MERQUAT 295 (trade name); Product of Ondeo Nalco Co.

TABLE 3

|   | Ingredients (wt %) | Cationic charge density (meq/g) | Examples 7 | Examples 8 | Examples 9 |
|---|---|---|---|---|---|
| A | Sodium polyoxyethylene(2) laurylether sulfate | | 6.5 | 6.5 | 6.5 |
| B | Polyoxyethylene(4.5) laurylether carboxylic acid | | 3.3 | 3.3 | 3.3 |
| C | Diallyldimethylammonium chloride homopolymer *2 | 6.2 | 0.3 | | |
|   | Diallyldimethylammonium chloride-acrylic acid (97:3) copolymer *1 | 6.0 | | 0.3 | |
|   | Diallyldimethylammonium chloride-acrylic acid (80:20) copolymer *3 | 5.0 | | | 0.3 |
|   | Diallyldimethylammonium chloride-acrylamide (50:50) copolymer *4 | 3.1 | | | |
|   | Diallyldimethylammonium chloride-acrylic acid-acrylamide (45:17:38) copolymer *5 | 2.8 | | | |
|   | Hydroxyethylcellulose hydroxypropyltrimethylammonium chloride ether (molecular weight: 400,000; "CATICELLO H-60", trade name; product of Kao Corporation) | 1.5 | | | |
|   | o-[2-hydroxy-3-(trimethylammonio)propyl] Guar Gum chloride ("JAGUAR C17K", trade name; product of Rhodia Inc.) | 1.6 | | | |
|   | Alkyl (C9-C13) glycoside | | 2.5 | 2.5 | 2.5 |
|   | Lauramidopropyl betaine | | 2.5 | 2.5 | 2.5 |
|   | 2-Ethylhexyl glyceryl ether | | 1.5 | 1.5 | 1.5 |
|   | Dipropylene glycol | | 5.0 | 5.0 | 5.0 |
| F | Ethylene glycol distearate (pearlescent agent) | | 2.0 | 2.0 | 2.0 |
|   | Sodium hydroxide (48%) | | 0.4 | 0.4 | 0.4 |
|   | Deionized water | | Balance | Balance | Balance |
|   | Total | | 100 | 100 | 100 |
|   | pH | | 6.3 | 6.4 | 6.2 |
|   | Speed until stop feeling was sensed in the course of rinsing | | 3 | 4 | 4 |
|   | Strength of stop feeling upon completion of rinsing | | B | A | B |
|   | Refreshed feeling after towel blotting | | B | B | B |
|   | Foam volume (cm) | | 3.9 | 4.3 | 3.6 |

*1: MERQUAT 295 (trade name); Product of Ondeo Nalco Co.
*2: MERQUAT 100 (trade name); Product of Ondeo Nalco Co.
*3: MERQUAT 280 (trade name); Product of Ondeo Nalco Co.
*4: MERQUAT 550 (trade name); Product of Ondeo Nalco Co.
*5: MERQUAT PLUS 3331 (trade name); Product of Ondeo Nalco Co.

TABLE 4

|   | Ingredients (wt %) | Cationic charge density (meq/g) | Comparative Examples 7 | 8 | 9 | 10 | 11 |
|---|---|---|---|---|---|---|---|
| A | Sodium polyoxyethylene(2) laurylether sulfate | | 6.5 | 6.5 | 6.5 | 6.5 | 6.5 |
| B | Polyoxyethylene(4.5) laurylether carboxylic acid | | 3.3 | 3.3 | 3.3 | 3.3 | 3.3 |
| C | Diallyldimethylammonium chloride homopolymer *2 | 6.2 | | | | | |
|   | Diallyldimethylammonium chloride-acrylic acid (97:3) copolymer *1 | 6.0 | | | | | |
|   | Diallyldimethylammonium chloride-acrylic acid (80:20) copolymer *3 | 5.0 | | | | | |

TABLE 4-continued

|  | Ingredients (wt %) | Cationic charge density (meq/g) | Comparative Examples | | | | |
|---|---|---|---|---|---|---|---|
|  |  |  | 7 | 8 | 9 | 10 | 11 |
|  | Diallyldimethylammonium chloride-acrylamide (50:50) copolymer *4 | 3.1 | 0.3 | | | | |
|  | Diallyldimethylammonium chloride-acrylic acid-acrylamide (45:17:38) copolymer *5 | 2.8 | | 0.3 | | | |
|  | Hydroxyethylcellulose hydroxypropyltrimethylammonium chloride ether (molecular weight: 400,000; "CATICELLO H-60", trade name; product of Kao Corporation) | 1.5 | | | 0.3 | | |
|  | o-[2-ydroxy-3-(trimethylammonio)propyl] Guar Gum chloride ("JAGUAR C17K", trade name; product of Rhodia Inc.) | 1.6 | | | | 0.3 | |
|  | Alkyl (C9-C13) glycoside | | 2.5 | 2.5 | 2.5 | 2.5 | 2.5 |
|  | Lauramidopropyl betaine | | 2.5 | 2.5 | 2.5 | 2.5 | 2.5 |
|  | 2-Ethylhexyl glyceryl ether | | 1.5 | 1.5 | 1.5 | 1.5 | 1.5 |
|  | Dipropylene glycol | | 5.0 | 5.0 | 5.0 | 5.0 | 5.0 |
| F | Ethylene glycol distearate (pearlescent agent) | | 2.0 | 2.0 | 2.0 | 2.0 | 2.0 |
|  | Sodium hydroxide (48%) | | 0.4 | 0.4 | 0.4 | 0.4 | 0.4 |
|  | Deionized water | | Balance | Balance | Balance | Balance | Balance |
|  | Total | | 100 | 100 | 100 | 100 | 100 |
|  | pH | | 6.3 | 6.4 | 6.3 | 6.3 | 6.3 |
|  | Speed until stop feeling was sensed in the course of rinsing | | 2 | 2 | 2 | 1 | 2 |
|  | Strength of stop feeling upon completion of rinsing | | C | D | C | D | C |
|  | Refreshed feeling after towel blotting | | A | A | A | C | C |
|  | Foam volume (cm) | | 3.4 | 3.3 | 3.4 | 4.4 | 1.8 |

*1: MERQUAT 295 (trade name); Product of Ondeo Nalco Co.
*2: MERQUAT 100(trade name); Product of Ondeo Nalco Co.
*3: MERQUAT 280(trade name); Product of Ondeo Nalco Co.
*4: MERQUAT 550(trade name); Product of Ondeo Nalco Co.
*5: MERQUAT PLUS 3331(trade name); Product of Ondeo Nalco Co.

TABLE 5

|  | Ingredients (wt %) | Cationic charge density (meq/g) | Examples | | | | | | |
|---|---|---|---|---|---|---|---|---|---|
|  |  |  | 10 | 11 | 12 | 13 | 14 | 15 | 16 |
| A | Sodium polyoxyethylene(2) laurylether sulfate | | 6.5 | 6.5 | 6.5 | 6.5 | | 6.5 | 6.5 |
|  | Sodium polyoxyethylene(1) laurylether sulfate | | | | | | 6.5 | | |
| B | Polyoxyethylene(4.5) laurylether carboxylic acid | | 3.3 | 3.3 | 3.3 | 3.3 | 3.3 | | 3.3 |
|  | Polyoxyethylene(2.5) laurylether carboxylic acid | | | | | | | 3.3 | |
| C | Diallyldimethylammonium chloride homopolymer *2 | 6.2 | | | | | | | |
|  | Diallyldimethylammonium chloride-acrylic acid (97:3) copolymer *1 | 6.0 | 0.1 | 0.2 | 0.4 | 0.1 | 0.1 | 0.1 | 0.7 |
|  | Diallyldimethylammonium chloride-acrylic acid (80:20) copolymer *3 | 5.0 | | | | | | | |
|  | Polyvinylpyrrolidone (K-value: 30) | | 0.3 | 0.2 | 0.04 | 0.3 | 0.3 | 0.3 | |
|  | Diallyldimethylammonium chloride-acrylamide (50:50) copolymer *4 | 3.1 | | | | | | | |
|  | Diallyldimethylammonium chloride-acrylic acid-acrylamide (45:17:38) copolymer *5 | 2.8 | | | | | | | |
|  | Hydroxyethylcellulose hydroxypropyltrimethylammonium chloride ether (molecular weight: 400,000; "CATICELLO H-60", trade name; product of Kao Corporation) | 1.5 | | | | | | | |
|  | o-[2-hydroxy-3-(trimethylammonio)propyl] Guar Gum chloride ("JAGUAR C17K", trade name; product of Rhodia Inc.) | 1.6 | | | | | | | |
|  | Alkyl(C9-C13) glycoside | | 2.5 | 2.5 | 2.5 | 2.5 | 2.5 | 2.5 | 2.5 |
|  | Lauramidopropyl betaine | | 2.5 | 2.5 | 2.5 | 2.5 | 2.5 | 2.5 | 2.5 |
|  | 2-Ethylhexyl glyceryl ether | | 1.5 | 1.5 | 1.5 | 1.5 | 1.5 | 1.5 | 1.5 |
|  | Dipropylene glycol | | 5.0 | 5.0 | 5.0 | 5.0 | 5.0 | 5.0 | 5.0 |
| F | Ethylene glycol distearate (pearlescent agent) | | 2.0 | 2.0 | 2.0 | 2.0 | 2.0 | 2.0 | 2.0 |
|  | Sodium hydroxide (48%) | | 0.4 | 0.4 | 0.4 | 0.4 | 0.4 | 0.4 | 0.4 |
|  | Deionized water | | Balance | Balance | Balance | Balance | Balance | Balance | Balance |
|  | Total | | 100 | 100 | 100 | 100 | 100 | 100 | 100 |
|  | pH | | 6.2 | 6.3 | 6.4 | 6.2 | 6.2 | 6.2 | 6.1 |
|  | Speed until stop feeling was sensed in the course of rinsing | | 4 | 4 | 3 | 3 | 4 | 4 | 4 |
|  | Strength of stop feeling upon completion of rinsing | | A | A | A | A | A | A | A |
|  | Refreshed feeling after towel blotting | | A | A | A | A | A | A | B |

TABLE 5-continued

| Ingredients (wt %) | Cationic charge density (meq/g) | Examples 10 | 11 | 12 | 13 | 14 | 15 | 16 |
|---|---|---|---|---|---|---|---|---|
| Foam volume (cm) | | 3.9 | 4.3 | 3.7 | 3.8 | 4.5 | 4.7 | 4.0 |
| Pearly appearance | | A | A | B | B | A | A | C |

*1: MERQUAT 295 (trade name); Product of Ondeo Nalco Co.
*2: MERQUAT 100(trade name); Product of Ondeo Nalco Co.
*3: MERQUAT 280(trade name); Product of Ondeo Nalco Co.
*4: MERQUAT 550(trade name); Product of Ondeo Nalco Co.
*5: MERQUAT PLUS 3331(trade name); Product of Ondeo Nalco Co.

TABLE 6

| | Ingredients (wt %) | Example 17 | Comparative Examples 12 | 13 |
|---|---|---|---|---|
| A | Sodium polyoxyethylene(2) laurylether sulfate | 6.5 | 6.5 | 6.5 |
| B | Polyoxyethylene(4.5) laurylether carboxylic acid | 3.3 | | |
| | Potassium myristate | | 3.3 | |
| | Acylglycine potassium | | | 3.3 |
| C | Diallyldimethylammonium chloride-acrylic acid (97:3) copolymer (cationic charge density: 6.0) *1 | 0.1 | 0.1 | 0.1 |
| C | Polyvinylpyrrolidone (K-value: 30) | 0.3 | 0.3 | 0.3 |
| | Alkyl(C9-C13) glycoside | 2.5 | 2.5 | 2.5 |
| | Lauramidopropyl betaine | 2.5 | 2.5 | 2.5 |
| | 2-Ethylhexyl glyceryl ether | 1.5 | 1.5 | 1.5 |
| E | Lauric acid | 0.5 | | |
| E | Myristyl alcohol | 0.5 | | |
| | Dipropylene glycol | 5.0 | 5.0 | 5.0 |
| F | Ethylene glycol distearate (pearlescent agent) | 2.0 | 2.0 | 2.0 |
| | Sodium hydroxide (48%) | 0.4 | | |
| | Deionized water | Balance | Balance | Balance |
| | Total | 100 | 100 | 100 |
| | pH | 6.4 | 9.6 | 8.5 |
| | Speed until stop feeling was sensed in the course of rinsing | 4 | 4 | 1 |
| | Strength of stop feeling upon completion of rinsing | A | A | D |
| | Refreshed feeling after towel blotting | A | D | D |
| | Foam volume (cm) | 3.6 | 1.3 | 1.6 |
| | Foam drainability (cm) | 2.5 | 2.8 | 3.6 |

*1: MERQUAT 295 (trade name); Product of Ondeo Nalco Co.

TABLE 7

| | Ingredients (wt %) | Examples 18 | 19 | 20 | 21 | 22 |
|---|---|---|---|---|---|---|
| A | Sodium polyoxyethylene(2) laurylether sulfate | 6.5 | 6.5 | 6.5 | 6.5 | 6.5 |
| B | Polyoxyethylene(4.5) laurylether carboxylic acid | 3.3 | 3.3 | 3.3 | 3.3 | 3.3 |
| C | Polyvinylpyrrolidone (K-value: 30) | 0.3 | | 0.05 | 0.5 | 0.8 |
| | Polyvinylpyrrolidone (K-value: 90) | | 0.3 | | | |
| | Alkyl(C9-C13) glycoside | 2.5 | 2.5 | 2.5 | 2.5 | 2.5 |
| | Lauramidopropyl betaine | 2.5 | 2.5 | 2.5 | 2.5 | 2.5 |
| | 2-Ethylhexyl glyceryl ether | 1.5 | 1.5 | 1.5 | 1.5 | 1.5 |
| | Dipropylene glycol | 5.0 | 5.0 | 5.0 | 5.0 | 5.0 |
| F | Ethylene glycol distearate (pearlescent agent) | 2.0 | 2.0 | 2.0 | 2.0 | 2.0 |
| | Sodium hydroxide (48%) | 0.4 | 0.4 | 0.4 | 0.4 | 0.4 |
| | Deionized water | Balance | Balance | Balance | Balance | Balance |
| | Total | 100 | 100 | 100 | 100 | 100 |
| | pH | 6.4 | 6.4 | 6.3 | 6.4 | 6.2 |
| | Appearance | Clear | Clear | Clear | Clear | Clear |
| | Pearly appearance | A | A | A | A | A |
| | Speed until stop feeling was sensed in the course of rinsing | 4 | 4 | 3 | 4 | 3 |
| | Strength of stop feeling upon completion of rinsing | A | B | B | A | A |

TABLE 7-continued

|  | Examples | | | | |
| --- | --- | --- | --- | --- | --- |
| Ingredients (wt %) | 18 | 19 | 20 | 21 | 22 |
| Smooth feeling after drying | A | A | B | A | B |
| Foam volume (cm) | 4.3 | 3.2 | 3.4 | 3.7 | 4.3 |

TABLE 8

| | Ingredients (wt %) | Examples | | | | | |
| --- | --- | --- | --- | --- | --- | --- | --- |
| | | 23 | 24 | 25 | 26 | 27 | 28 |
| A | Sodium polyoxyethylene(2) laurylether sulfate | 8.3 | 2.5 | 3.3 | 16.5 | | 6.5 |
| | Sodium polyoxyethylene(1) laurylether sulfate | | | | | 6.5 | |
| B | Polyoxyethylene(4.5) laurylether carboxylic acid | 1.5 | 7.4 | 1.7 | 8.5 | 3.3 | |
| | Polyoxyethylene(2.5) laurylether carboxylic acid | | | | | | 3.3 |
| C | Polyvinylpyrrolidone (K-value: 30) | 0.3 | 0.3 | 0.3 | 0.3 | 0.3 | 0.3 |
| | Alkyl(C9-C13) glycoside | 2.5 | 2.5 | 2.5 | 2.5 | 2.5 | 2.5 |
| | Lauramidopropyl betaine | 2.5 | 2.5 | 2.5 | 2.5 | 2.5 | 2.5 |
| | 2-Ethylhexyl glyceryl ether | 1.5 | 1.5 | 1.5 | 1.5 | 1.5 | 1.5 |
| | Dipropylene glycol | 5.0 | 5.0 | 5.0 | 5.0 | 5.0 | 5.0 |
| F | Ethylene glycol distearate (pearlescent agent) | 2.0 | 2.0 | 2.0 | 2.0 | 2.0 | 2.0 |
| | Sodium hydroxide (48%) | | 0.9 | 0.2 | 1.0 | 0.4 | 0.3 |
| | Deionized water | Balance | Balance | Balance | Balance | Balance | Balance |
| | Total | 100 | 100 | 100 | 100 | 100 | 100 |
| | pH | 6.3 | 5.9 | 6.3 | 5.8 | 6.4 | 5.9 |
| | Appearance | Clear | Clear | Clear | Clear | Clear | Clear |
| | Pearly appearance | A | A | A | A | A | A |
| | Speed until stop feeling was sensed in the course of rinsing | 3 | 3 | 4 | 3 | 4 | 3 |
| | Strength of stop feeling upon completion of rinsing | B | A | A | A | A | A |
| | Smooth feeling after drying | B | A | B | B | A | A |
| | Foam volume (cm) | 2.8 | 3.3 | 2.6 | 4.4 | 4.8 | 3.9 |

TABLE 9

| | Ingredients (wt %) | Examples | | | |
| --- | --- | --- | --- | --- | --- |
| | | 29 | 30 | 31 | 32 |
| A | Sodium polyoxyethylene(2) laurylether sulfate | 6.5 | 6.5 | 6.5 | 6.5 |
| B | Polyoxyethylene(4.5) laurylether carboxylic acid | 3.3 | 3.3 | 3.3 | 3.3 |
| C | Polyvinylpyrrolidone (K-value: 30) | 0.3 | 0.3 | 0.3 | 0.3 |
| | Alkyl(C9-C13) glycoside | | 2.5 | 2.5 | 2.5 |
| | Lauramidopropyl betaine | 2.5 | | 2.5 | 2.5 |
| | 2-Ethylhexyl glyceryl ether | 1.5 | 1.5 | | 1.5 |
| | Dipropylene glycol | 5.0 | 5.0 | 5.0 | |
| F | Ethylene glycol distearate (pearlescent agent) | 2.0 | 2.0 | 2.0 | 2.0 |
| | Sodium hydroxide (48%) | 0.4 | 0.4 | 0.4 | 0.4 |
| | Deionized water | Balance | Balance | Balance | Balance |
| | Total | 100 | 100 | 100 | 100 |
| | pH | 6.4 | 6.2 | 6.2 | 6.4 |
| | Appearance | Clear | Clear | Clear | Clear |
| | Pearly appearance | A | A | A | A |
| | Speed until stop feeling was sensed in the course of rinsing | 4 | 4 | 4 | 4 |
| | Strength of stop feeling upon completion of rinsing | A | A | A | A |
| | Smooth feeling after drying | A | A | A | A |
| | Foam volume (cm) | 2.5 | 2.5 | 2.6 | 3.4 |

Example 33

A body shampoo of the formula shown below was prepared as in Examples 1 to 32.

TABLE 10

| | (Ingredients) | (wt %) |
| --- | --- | --- |
| A | Sodium polyoxyethylene(2) laurylether sulfate | 6.5 |
| B | Polyoxyethylene(4.5) laurylether carboxylic acid | 3.3 |

TABLE 10-continued

| | (Ingredients) | (wt %) |
| --- | --- | --- |
| C | Diallyldimethylammonium chloride-acrylic acid (97:3) copolymer (cationic charge density: 6.0) *1 | 0.4 |
| D | Sodium chloride | 1.0 |
| D | Sodium malate | 1.5 |
| | Alkyl(C9-13) glycoside | 2.5 |
| | Lauramidopropyl betaine | 2.5 |
| | Alkyl(8) glyceryl ether | 1.5 |

TABLE 10-continued

| | (Ingredients) | (wt %) |
|---|---|---|
| E | Lauric acid | 0.5 |
| | Dipropylene glycol | 1.0 |
| F | Ethylene glycol distearate (pearlescent agent) | 2.0 |
| | Sodium hydroxide (48%) | 0.4 |
| | Deionized water | Balance |
| Total | | 100 |
| pH | | 6.2 |

*1: MERQUAT 295 (trade name); Product of Ondeo Nalco Co.

Example 34

A body shampoo of the formula shown below was prepared as in Examples 1 to 32.

TABLE 11

| | (Ingredients) | (wt %) |
|---|---|---|
| A | Sodium polyoxyethylene(2) laurylether sulfate | 6.5 |
| B | Polyoxyethylene(4.5) laurylether carboxylic acid | 3.3 |
| C | Diallyldimethylammonium chloride-acrylic acid (97:3) copolymer (cationic charge density: 6.0) *1 | 0.4 |
| D | Sodium chloride | 1.0 |
| D | Sodium lactate | 1.0 |
| | Alkyl(C9-13) glycoside | 2.5 |
| | Lauramidopropyl betaine | 2.5 |
| | Alkyl(8) glyceryl ether | 1.5 |
| E | Lauric acid | 0.5 |
| | Dipropylene glycol | 1.0 |
| F | Ethylene glycol distearate (pearlescent agent) | 2.0 |
| | Sodium hydroxide (48%) | 0.4 |
| | Deionized water | Balance |
| Total | | 100 |
| pH | | 6.2 |

*1: MERQUAT 295 (trade name); Product of Ondeo Nalco Co.

Example 35

A body shampoo of the formula shown below was prepared as in Examples 1 to 32.

TABLE 12

| | (Ingredients) | (wt %) |
|---|---|---|
| A | Sodium polyoxyethylene(2) laurylether sulfate | 6.5 |
| B | Polyoxyethylene(4.5) laurylether carboxylic acid | 3.3 |
| C | Diallyldimethylammonium chloride-acrylic acid (97:3) copolymer (cationic charge density: 6.0)*1 | 0.4 |
| D | Sodium chloride | 1.0 |
| D | Sodium succinate | 1.5 |
| | Alkyl(C9-13) glycoside | 2.5 |
| | Lauramidopropyl betaine | 2.5 |
| | Alkyl(8) glyceryl ether | 1.5 |
| E | Lauric acid | 0.5 |
| | Dipropylene glycol | 1.0 |
| F | Ethylene glycol distearate (pearlescent agent) | 2.0 |
| | Sodium hydroxide (48%) | 0.4 |
| | Deionized water | Balance |
| Total | | 100 |
| pH | | 6.2 |

*1: MERQUAT 295 (trade name); Product of Ondeo Nalco Co.

Example 36

A body shampoo of the formula shown below was prepared as in Examples 1 to 32.

TABLE 13

| | (Ingredients) | (wt %) |
|---|---|---|
| A | Sodium polyoxyethylene(2) laurylether sulfate | 6.5 |
| B | Polyoxyethylene(4.5) laurylether carboxylic acid | 3.3 |
| C | Diallyldimethylammonium chloride-acrylic acid (97:3) copolymer (cationic charge density: 6.0) *1 | 0.4 |
| D | Sodium chloride | 1.0 |
| D | Sodium citrate | 2.5 |
| | Alkyl(C9-13) glycoside | 2.5 |
| | Lauramidopropyl betaine | 2.5 |
| | Alkyl(8) glyceryl ether | 1.5 |
| E | Lauric acid | 0.5 |
| | Dipropylene glycol | 1.0 |
| F | Ethylene glycol distearate (pearlescent agent) | 2.0 |
| | Sodium hydroxide (48%) | 0.4 |
| | Deionized water | Balance |
| Total | | 100 |
| pH | | 6.2 |

*1: MERQUAT 295 (trade name); Product of Ondeo Nalco Co.

The body shampoos obtained in Examples 33 to 36 were all excellent in formability and foam quality and good in stop feeling during rinsing and refreshed feeling after towel blotting. They were also good in pearly appearance.

The invention claimed is:

1. A skin cleansing composition comprising the following ingredients (A), (B) and (C):(A) a polyoxyethylene alkylether sulfate, (B) a polyoxyethylene alkylether carboxylate, and (C) a cationic group-containing polymer having a cationic charge density of not less than 4.5 meq/g, and/or polyvinylpyrrolidone, wherein a weight ratio (A):(B) of the ingredient (A) to the ingredient (B) is from 85:15 to 25:75, a total content of the ingredients (A) and (B) based on the whole composition ranges from 5 to 25 wt %, and a content of the ingredient (C) ranges from 0.05 to 1 wt %.

2. The skin cleansing composition according to claim 1, wherein the cationic group-containing polymer as an ingredient (C) is a homopolymer of dimethyldiallylammonium chloride or a copolymer of dimethyldiallylammonium chloride and acrylic acid.

3. The skin cleansing composition according to claim 1 or 2, further comprising, as an ingredient (D), an inorganic salt or an organic acid salt having not more than 6 carbon atoms.

4. The skin cleansing composition according to any one of claims 1 to 2, further comprising, as an ingredient (E), a higher fatty acid or higher alcohol.

5. The skin cleansing composition according to any one of claims 1 to 2, further comprising, as an ingredient (F), a pearlescence-imparting agent.

6. The skin cleansing composition according to any one of claims 1 to 2 which has a pH of from 4.5 to 7 when diluted to 20-fold by weight with deionized water.

7. The skin cleansing composition according to claim 1, wherein said polyoxyethylene alkylether sulfate is represented by the following formula

$$R\text{—}O(CH_2CH_2O)_n\text{—}SO_3X$$

wherein R represents an alkyl or alkenyl group having from 10 to 18 carbon atoms, n stands for a number of from 0.5 to 5 on average, and X represents a hydrogen atom, alkali metal, alkaline earth metal, ammonium or organic ammonium.

8. The skin cleansing composition according to claim 7, wherein R is an alkyl group having from 12 to 14 carbon atoms and n is from 1 to 4.

9. The skin cleansing composition according to claim 1, wherein (A) is contained in an amount of from 1 to 20 wt %.

10. The skin cleansing composition according to claim 1, wherein said polyoxyethylene alkylether carboxylate is represented by the following formula

wherein R represents an alkyl or alkenyl group having from 10 to 18 carbon atoms, n stands for a number of from 0.5 to 10 on average, and X represents a hydrogen atom, alkali metal, alkaline earth metal, ammonium or organic ammonium.

11. The skin cleansing composition according to claim 9, wherein R is an alkyl group having from 12 to 16 carbon atoms and n is from 1 to 6.

12. The skin cleansing composition according to claim 1, wherein (B) is contained in an amount of from 1 to 20 wt %.

13. The skin cleansing composition according to claim 1, wherein said cationic charge density is from 4.5 to 7 meq/g.

14. The skin cleansing composition according to claim 1, wherein said cationic group-containing polymer is at least one polymer selected from the group consisting of a dimethyldiallylammonium chloride; a copolymer of dimethyldiallylammonium chloride with other monomers and polychloromethacryloyloxyethyltrimethylammonium chloride.

15. The skin cleansing composition according to claim 1, comprising said cationic group-containing polymer and said polyvinylpyrrolidone in a weight ratio of cationic group-containing polymer whose cationic charge density is not less than 4.5 meq/g to polyvinylpyrrolidone of from 90:10 to 20:80.

16. The skin cleansing composition according to claim 15, wherein said ratio is from 80:20 to 25:75.

17. The skin cleansing composition according to claim 3, wherein ingredient (D) present in an amount of from 0.5 to 10 wt %.

18. The skin cleansing composition according to claim 1, wherein a value of (C)/((A)+(B)) is from 0.025 to 0.08.

19. The skin cleansing composition according to claim 3, wherein a value of (D)/((A)+(B)+(C)) is from 0.19 to 0.34.

20. The skin cleansing composition according to claim 4, wherein ingredient (E) is present in an amount of from 0.3 to 3 wt %.

21. The skin cleansing composition according to claim 5, wherein ingredient (F) is present in an amount of from 1 to 3 wt %.

* * * * *